(12) United States Patent
Yu

(10) Patent No.: US 7,229,782 B1
(45) Date of Patent: Jun. 12, 2007

(54) ANTIBODIES SPECIFIC TO MULTIPLE BETA BLOCKERS AND METHODS FOR THEIR USE

(75) Inventor: Liuming Yu, Leawood, KS (US)

(73) Assignee: LabOne, Inc., Lenexa, KS (US)

( * ) Notice: Subject to any disclaimer, the term of this patent is extended or adjusted under 35 U.S.C. 154(b) by 367 days.

(21) Appl. No.: 10/910,154

(22) Filed: Aug. 3, 2004

(51) Int. Cl.
*G01N 33/535* (2006.01)
*G01N 33/533* (2006.01)
*C07K 16/44* (2006.01)
*C07K 17/06* (2006.01)

(52) U.S. Cl. .................. 435/7.92; 435/7.9; 435/7.93; 436/544; 436/545; 436/546; 530/388.9; 530/389.8; 530/403; 530/404; 530/405; 530/406

(58) Field of Classification Search ............ 530/388.9, 530/403, 389.8, 404, 405, 406; 435/7.9, 435/7.92, 7.93; 436/544, 545, 546
See application file for complete search history.

(56) References Cited

U.S. PATENT DOCUMENTS

| | | | | |
|---|---|---|---|---|
| 4,070,492 A | * | 1/1978 | Spector | 436/542 |
| 4,329,502 A | * | 5/1982 | Singh et al. | 564/349 |
| 4,332,787 A | * | 6/1982 | Homcy et al. | 436/542 |
| 4,472,301 A | * | 9/1984 | Buckler et al. | 530/363 |
| 4,786,594 A | | 11/1988 | Khanna et al. | |
| 5,045,452 A | | 9/1991 | Spragg et al. | |
| 5,338,659 A | | 8/1994 | Kauvar et al. | |
| 5,527,686 A | | 6/1996 | Fitzpatrick et al. | |
| 6,406,667 B1 | | 6/2002 | Singh et al. | |
| 6,498,010 B1 | | 12/2002 | Fitzgerald et al. | |
| 6,617,116 B2 | | 9/2003 | Guan et al. | |
| 2002/0160538 A1 | | 10/2002 | Guirguis | |
| 2003/0198976 A1 | | 10/2003 | Feder et al. | |

OTHER PUBLICATIONS

L. Wang et al, FEBS Letters (1986), vol. 199(2), 173-178.*
S. Chamat et al, J. of Immunology (1984), vol. 133(3), 1547-1552.*
S. Chu et al, J. Pharmaceutical Sciences, vol. 70(9), 990-994.*
Neogen Corporation, Elisa Kit Instructions Product #107319, 2001, Lansing, MI.
Orasure Technologies, Inc., Auto-Lyte® Beta Blockers EIA, 2000, Bethlehem, PA.
Hoebeke et al., The Production and characterization of antibodies against β-adrenergic antagonists. Biochemical Pharmacology, 27:1527-1532, 1978.

* cited by examiner

*Primary Examiner*—Mary E. Ceperley
(74) *Attorney, Agent, or Firm*—Foley & Lardner, LLP

(57) ABSTRACT

The present invention is directed antibodies specific to multiple beta blockers, as well as immunogens used to produce the antibodies and immunoassay kits and methods for using the antibodies.

22 Claims, No Drawings

ANTIBODIES SPECIFIC TO MULTIPLE BETA BLOCKERS AND METHODS FOR THEIR USE

CROSS-REFERENCE TO RELATED APPLICATIONS

Not Applicable.

STATEMENT REGARDING FEDERALLY SPONSORED RESEARCH OR DEVELOPMENT

Not applicable.

BACKGROUND OF THE INVENTION

1. Field of the Invention

The present invention is directed antibodies specific to multiple beta blockers, as well as immunogens used to produce the antibodies, and immunoassay kits and methods for using the antibodies.

2. Description of Related Art

Beta blockers are a class of commonly-prescribed drugs used in the management of individuals with high blood pressure, congestive heart failure, abnormal heart rhythms and chest pain. Presently, more than ten different beta blockers are available, all by prescription. Currently available beta blockers include Atenolol (4-[2-Hydroxy-3-[(1-methylethyl)amino]propoxy]benzeneacetamide), Metoprolol (1-[4-(2-Methoxyethyl)phenoxy]-3-[(1-methylethyl) amino]-2-propanol), Bisoprolol (1-[4-[[2-(1-Methylethoxy) ethoxy]-methyl]phenoxy]-3-[(1-methylethyl)amino]-2-propanol), Acebutolol N-[3-Acetyl-4-[2-hydroxy-3-[(1-methylethyl)amino]propoxy]phenyl]butanamide), Esmolol (4-[2-Hydroxy-3-[(1-methylethyl)amino]propoxy]benzenepropanoic acid methyl ester), Propranolol (1-[(1-Methylethyl)amino]-3-(1-napthalenyloxy)-2-propanol), Pindolol (1-(1H-Indol-4-yloxy)-3-[(1-methylethyl)amino]-2-propanol), Timolol ((S)-1-[(1,1-Dimethylethyl)amino]-3-[[4-(4-morpholinyl)-1,2,5-thiadiazol-3-yl]oxy]-2-propanol) and Nadolol (5-[3-[(1,1, -Dimethylethyl)amino]-2-hyroxypropoxy]-1,2,3,4-tetrahydro-2,3-naphthalenediol). According to RxList.com, the following four beta blockers were the most prescribed beta blockers in 2002: Atenolol, Metoprolol, Bisoprolol and Propranolol. These drugs were ranked $3^{rd}$, $19^{th}$, $139^{th}$ and $140^{th}$, respectively, in the top 200 prescriptions for 2002 based on the number of US prescriptions dispensed.

Detection of beta blockers in physiological fluids is often desirable. For example, insurance companies often wish to test for beta blockers as part of their screening processes. Thus, a method for detecting beta blockers in physiological fluids is needed.

Various techniques have been employed to detect drugs in physiological samples, including gas-liquid chromatography, mass spectroscopy, fluorometry and immunoassays. Immunoassays are widely used to detect drugs in physiological samples because such assays are inexpensive and can be performed rapidly. Immunoassays detect chemical substances in a sample using highly specific binding between an antibody and the target chemical. Thus, in order to have the desired specificity, immunoassays are normally specific for a single drug. It is difficult to develop an antibody that will bind to a class of drugs, yet not bind to other drugs and substances that may be present in a sample.

Currently, no known immunoassay detects multiple beta blockers that may exist in a sample. Rather, in commercially available beta blocker immunoassays, the antibody used in the test is specific to a single beta blocker. For example, various antibodies are specific to Propranolol, but unreactive with other beta blockers. In addition, for a majority of beta blockers, there is currently no immunoassay available. As a result, the most commonly prescribed beta blockers, such as Atenolol and Metoprolol, are not detectable by any currently available immunoassay. Thus, a need remains for a test that can detect a variety of the commonly-available beta blockers in a single immunoassay.

BRIEF SUMMARY OF THE INVENTION

The present invention is directed antibodies specific to multiple beta blockers, as well as immunogens used to produce the antibodies and immunoassay kits and methods for using the antibodies. The immunogen of the present invention is comprised of a novel beta blocker derivative core structure, as follows:

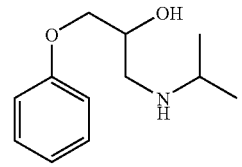

The beta blocker derivative is coupled to an immunogenic carrier via a linkage, to produce the immunogen of the present invention, with the following preferred structure:

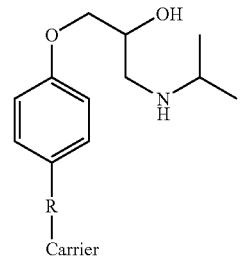

wherein Carrier is an immunogenic carrier and R is a linkage. Preferably R is a linking group, more preferably R is —(CH$_2$)$_n$COO—, wherein n is 0 to many. Most preferably R is —CH$_2$COO—. The beta blocker derivative core structure of the immunogen may be substituted, provided the immunogen retains its ability to produce an antibody specific to two or more beta blockers.

The immunogen of the present invention is used to produce antibodies specific to two or more beta blockers. Unlike known beta blocker antibodies that are specific to a single beta blocker, the antibodies of the present invention recognize multiple beta blockers and/or their metabolites, yet are not cross-reactive with non-beta blocker drugs, i.e. the antibodies of the present invention are specific to multiple beta blockers.

Preferably, an antibody of the present invention recognizes, at a minimum, two or more of the beta blockers selected from the group consisting of Atenolol, Metoprolol, Bisoprolol, Acebutolol, Esmolol, Propranolol, Pindolol, Timolol and Nadolol, more preferably from the group consisting of Atenolol, Metoprolol, Propranolol, Bisoprolol and Pindolol. More preferably, an antibody of the present invention recognizes, at a minimum, Atenolol and Metoprolol, the two most commonly prescribed beta blockers. For purposes of this invention, an antibody is considered specific to, or to recognize, a beta blocker if it is specific to, or recognizes, the beta blocker and/or its metabolites.

The present invention is also directed to an immunoassay kit and method for detecting multiple beta blockers in a sample. The assay kit and method detect a panel of beta blockers, yet have little cross-reactivity with non-beta blocker drugs. Preferably the immunoassay kit is comprised of an antibody of the present invention and one or more reagents. Preferably the immunoassay is a radioimmunoassay (RIA), a fluoroimmunoassay, or a gold labeled strip test, but more preferably is an enzyme immunoassay selected from the group consisting of ELISA and EMIT.

The beta blocker assay of the present invention can be used for a variety of purposes, including insurance or other drug screening of humans, testing for compliance with prescribed drug protocols, emergency room screening for patients presenting with acute myocardial infarction, and testing for banned beta blockers in performance animals.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

The present invention is directed antibodies specific to multiple beta blockers, as well as immunogens used to produce the antibodies and immunoassay kits and methods for using the antibodies. The immunogen of the present invention is comprised of a novel beta blocker derivative core structure, as follows:

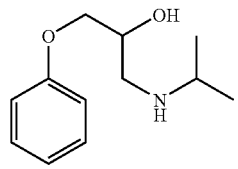

The beta blocker derivative is coupled to an immunogenic carrier via a linkage, to produce the immunogen of the present invention, with the following preferred structure:

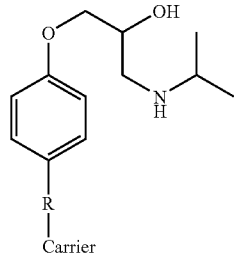

wherein Carrier is an immunogenic carrier and R is a linkage. The beta blocker derivative may be coupled to the immunogenic carrier through linkage R by any techniques known in the art or hereafter developed. Linkage R is preferably a linking group capable of linking the beta blocker derivative to the Carrier. Preferably, linkage R is —$(CH_2)_nCOO$—, wherein n is an integer from 0 to many. The value for n can be any number that will maintain the functionality of the linking group. Preferably n is between 0 and about 1000, more preferably is between 0 and about 100 and most preferably is between 0 and about 10. Most preferably R is —$CH_2COO$. Alternatively, R may be a linking group of —$(CH_2)_nNH$— or of —$(CH_2)_nO$—, where n is 0 to many, or R may be a direct linkage between the beta blocker derivative and the immunogenic carrier. In an alternative embodiment, linkage R may be located at any other position on the ring structure.

The immunogenic carrier can be any immunogenic carrier known in the art or hereafter developed. Preferably, the immunogenic carrier will be a protein or polypeptide, most preferably a protein, although other materials of sufficient size and immunogenicity can be used. Particularly preferred immunogenic carriers include albumin, hemocyanin (KLH), and thyroglobulin. The beta blocker derivative core structure of the immunogen may be substituted, provided the immunogen retains its ability to produce an antibody specific to two or more beta blockers. The substituents may include alkyl, alkenyl, alkynyl, aryl, heteroaryl, and/or may contain nitrogen, oxygen, sulfur, halogens, and include for example, lower alkyl such as methyl, ethyl or butyl, lower alkoxy, such as methoxy, ethoxy, or butoxy, halogen such as chloro or fluoro, nitro, amino and keto.

The immunogen of the present invention is used to produce an antibody specific to multiple beta blockers. As used herein, the term "multiple" means two or more. Preferably, an antibody of the present invention recognizes, at a minimum, two or more of the beta blockers selected from the group consisting of Atenolol, Metoprolol, Propranolol, Bisoprolol and Pindolol. More preferably, an antibody of the present invention recognizes, at a minimum, Atenolol and Metoprolol, the two most commonly prescribed beta blockers. It should be understood that as used herein, the term antibody refers not only to the complete antibody, but also to antibody fragments or derivatives, provided the binding properties of the complete antibody are maintained.

Antibodies of the present invention have binding specificity for two or more beta blockers. It should be understood that an antibody is considered specific to beta blockers although it may have some binding affinity for non-beta blocker compounds, provided the affinity for two or more beta blockers is measurably higher than the affinity for non-beta blocker compounds. For example, an antibody is considered specific to beta blockers if, at a specified analytical cut off point for an assay, the antibody will produce a positive test result for two or more beta blockers, but will not produce a positive result for samples which do not contain beta blockers but may contain other drug compounds.

Antibodies of the present invention may be produced using the immunogen of the invention using conventional techniques known in the art or hereafter developed. Antibodies of the present invention may be polyclonal or monoclonal and preferably are polyclonal. Thus, when used herein, the term "an antibody" would encompass a polyclonal antibody comprising multiple antibody species. Polyclonal antibodies are typically formed by inoculating a host animal, such a rabbit, goat, mouse, sheep, guinea pig or horse, at one or more sites with an immunogen, either alone or in combination with an adjuvant. Subsequent injections are made until the optimal titer is reached. The animal is bled to yield a suitable volume of specific antiserum, which may be purified. Monoclonal antibodies may be produced by somatic cell hybridization techniques, also well known in the art.

The present invention is also directed to an immunoassay methods using an antibody of the present invention to detect multiple beta blockers in a sample. Antibodies of the present invention may be used in any immunoassay methods known or hereafter developed. The immunoassay method of the present invention is preferably an enzyme immunoassay. Any enzyme immunoassay known in the art or hereafter developed may be used consistent with the present invention. The immunoassay method preferably comprises obtaining a sample to be tested, exposing the sample to the antibody of the present invention, and determining whether the antibody binds to the contents of said sample. If the antibody binds to the contents of the sample, it is an indication that the sample contains beta blockers. Preferably, the test is performed in vitro. The sample is preferably a fluid sample, more preferably a physiological sample, and most preferably a urine sample. The method may also comprise the testing of positive and negative control samples. Preferably the immunoassay method of the present invention is used as a qualitative test to detect the presence of beta blockers, although quantitative tests are contemplated by and within the scope of the present invention. The immunoassay method of the present invention may be performed manually or utilizing an automated machine. If an automated machine is used, the method may further comprise calibrating the machine.

In a preferred embodiment, the immunoassay of the present invention is used in an ELISA, EMIT or gold labeled strip test. In one type of ELISA (enzyme-linked immunosorbent assay), the sample to be tested is combined with an enzyme-beta blocker conjugate and run over a surface to which immobilized antibodies of the present invention have been attached. Any free beta blockers in the sample compete with the enzyme-beta blocker conjugate to bind to the antibody layer. The enzyme beta blocker conjugate bound to the antibody layer can be visualized by the addition of a substrate to the enzyme that changes color in the presence of the enzyme. Free beta blocker in the sample results in fewer enzyme-beta blocker conjugates bound to the antibody, which results in a smaller color change. The enzyme may be any enzyme known in the art or hereafter developed suitable for use in ELISA. Preferably the enzyme is horseradish peroxidase (HRP) and the beta blocker to which it is conjugated is Atenolol.

An EMIT (enzyme multiplied immunoassay) is a homogeneous immunoassay, based on the competition between the free beta blockers in the sample and beta blockers conjugated to an enzyme for the binding sites of the anti-beta blocker antibodies. The enzyme is conjugated to beta blockers that are recognized by the antibody. The enzyme may be any enzyme known in the art or hereafter developed suitable for use in EMIT assays. Preferably, the beta blockers are conjugated to Glucose-6-Phospahte Dehydrogenase ("G6PDH"). G6PDH converts glucose-6-phosphate (G6P) and oxidized nicotinamide adenine dinucleotide (NAD) to gluconate-6-phosphate and NADH, respectively, as follows:

$$G6P + NAD^+ \xrightarrow{G6PDH} Gluconate\text{-}6P + NADH + H^+$$

This process results in a change in absorbance, or a signal, measured at 340 nm.

The enzyme-beta blocker conjugate in the reagent is constituted in such a way that, as soon as the antibody of the present invention binds to the enzyme-beta blocker conjugate, the enzyme activity is inhibited. The beta blocker present in the sample competes with the conjugated beta blocker to bind to the antibody. Thus, if there is more beta blocker in the sample, there is more free enzyme-beta blocker conjugate and a stronger signal is produced.

Preferably, the method of the present invention is performed using an immunoassay kit. The immunoassay kit preferably comprises an antibody of the present invention and all elements needed to perform the desired immunoassay. Preferably the kit comprises one or more reagents for detecting a complex of the antibody and a beta blocker. The reagents may be any reagents known in the art. Preferably the reagents are selected from the group consisting of an enzyme, a radioisotope, a fluorescent reagent, a luminescent reagent and a chemiluminescent reagent. A kit for performing EMITs would preferably include an antibody of the present invention, an enzyme-beta blocker conjugate, and a substrate. In the preferred embodiment the enzyme is G6PDH and the substrate is G6P. In such embodiment, preferably the antibody and substrate are packaged as a first reagent, and the enzyme-beta blocker conjugate is packaged as a second reagent. Preferably the first reagent also contains $NAD^+$. A kit for performing ELISAs preferably includes a solid surface, such as beads, to which an antibody of the present invention is affixed, as well as a reagent comprising an enzyme-beta blocker conjugate. Additional buffers and components may be added to the reagents, as may be known in the art or hereafter developed. The kit may also include controls, preferably positive and negative controls, and a calibrator.

The following Examples illustrate the present invention.

EXAMPLE 1

Synthesis of an Immunogen of the Present Invention

The beta blocker derivative core structure of the present invention, with attached linking group, may be synthesized by hydrolysis of the beta blocker Atenolol, using standard organic synthesis techniques, as follows:

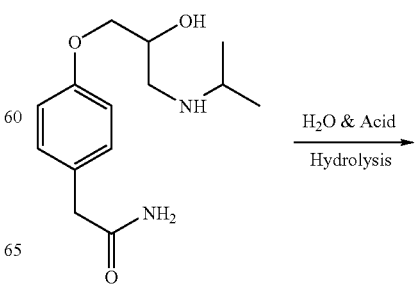

-continued

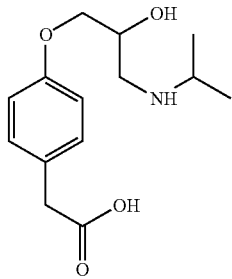

The beta blocker derivative core structure with attached linking group was conjugated to the carrier protein, as follows:

Bovine Serum Albumin (BSA) (300 mg) was dissolved into 60 ml 0.2 M Phosphate Buffer, pH=8.5. The following chemicals were added to a small beaker and stirred at room temperature to dissolve:

1). 300 mg Beta blocker derivative core structure with attached linking group.

2). 3 ml Reagent Alcohol (Allegiance).

3). 3 ml DMF (dimethylformamide) (Sigma).

4). 6 ml 10 mM Potassium Phosphate Buffer, pH=5.0.

5). 600 mg of 1-Ethyl-3-(–3-Dimethylaminopropyl) Carbodiimide (Sigma).

The resulting solution was added to the BSA solution dropwise while stirring and was stirred overnight at 2–8° C. The immunogen of the present invention was purified from the resulting solution by dialysis.

EXAMPLE 2

Production of Antibodies of the Present Invention

Production of antibodies of the present invention was performed using conventional methods. In brief, the immunogen of the present invention was diluted to 0.5 to 1.0 mg/ml in phosphate buffered saline (PBS). Then 0.5–1.0 ml of the immunogen solution was injected into a rabbit with complete Freunds adjuvant. After 2–3 weeks, the animal was injected with 0.5–1.0 ml of the same immunogen solution with incomplete Freunds adjuvant. The same injection was repeated every other week until acceptable titer was obtained.

EXAMPLE 3

Accuracy

Accuracy of the antibody of the present invention was assessed by testing 77 urine specimens from patients who had ingested Atenolol, Metoprolol or Propranolol within 24 hours, and 28 urine specimens from patients who had not ingested any beta blocker within 7 days. Accuracy refers to an estimate of the non-random systematic bias between samples of data or between a sample of data and the true population value.

Samples were checked for turbidity and growth. A homogeneous enzyme immunoassay was carried out on an Olympus AU-5200 analyzer using the following assay parameters:

| | |
|---|---|
| TEMPERATURE: | 37° C. |
| OPERATION: | YES |
| SAMPLE VOLUME: | 12 µl |
| REAGENT VOLUME R1: | 100 µl |
| R2: | 100 µl |
| METHOD: | END |
| WAVELENGTH 1: | 340 nm |
| 2: | 410 nm |
| REACTION SLOPE: | + |
| MEASURE POINT S: | 9 |
| E: | 16 |
| OD VALUE RANGE MAX.: | NOT APPLICABLE |
| MIN.: | NOT APPLICABLE |
| LIMIT OF LINEARITY: | NOT APPLICABLE |
| NORMAL VALUE H: | 2.5 |
| L: | 0 |
| REAGENT OD RANGE H: | 2.000 |
| L: | –2.000 |
| REAGENT PARAMETERS CALIBRATION TYPE: | AB |

Reagent 1 is comprised of a titer of 1–500 dilution of an antibody of the present invention, 11.25 mM NAD+, 11.25 mM G6P, 0.1% w/v sodium azide and 100 mM Tris.

Reagent 2 is comprised of a titer of 1–2000 dilution of a G6PDH-beta blocker conjugate, 0.1% w/v sodium azide, and 50 mM Tris.

A homogenous calibrator containing sodium azide was used to calibrate the analyzer prior to each run.

The analytical cutoff for the test was set at 5.0 µg Atenolol per ml of urine. The result was scored as a positive if the signal strength was greater than that produced by 5.0 µg Atenolol per ml of urine.

The results are shown in the following table:

| | True Positives (User of Beta-blocker) | True Negatives |
|---|---|---|
| Positive (≧5.0 µg/ml) | 58 | 0 |
| Negative | 19 | 28 |

An assay is sensitive if it correctly identifies positive samples as positive. The sensitivity can be measured by the proportion of true positives that are correctly identified calculated by dividing the number of true positives by the total number of true positives and false negatives. An assay is specific if it correctly identifies negative samples as negatives. The specificity can be measured by the proportion of true negatives that are correctly identified, calculated by dividing the number of true negatives by the total number of true negatives and false positives. Based on these results, the immunoassay of the present invention had a specificity of 100.0% (i.e. no-false positives) and a sensitivity of 75.3%.

EXAMPLE 4

The test of Example 3 was performed using different cutoffs and/or using a Stabilur tablet preservative. The results are set forth in the following table:

| Cutoff (μg Atenolol/ml urine) | Preservative? | Specificity | Sensitivity |
|---|---|---|---|
| 2.5 | N | 87.0% | 100.0% |
| 2.5 | Y | 81.8% | 100.0% |
| 5.0 | Y | 68.8% | 100.0% |

EXAMPLE 5

Precision

Precision measures the repeatability of an analytical technique. Its opposite is imprecision. Imprecision is expressed as the percentage coefficient of variation (% CV).

One negative urine specimen and one positive urine specimen were used in this study. Each specimen was tested ten (10) times per run, for a total of five (5) runs, using the procedure described in Example 3. The intra assay mean CV was 11.2%. The inter-assay mean optical density reading CV was 13.1%.

EXAMPLE 5

Interference from Other Drugs

Interference from other drugs was tested using fifty-five (55) frequently used chemicals and medicines, at concentrations of 10.0 μg/ml urine. The chemicals tested are listed in the following table:

| ID# | Chemical Name | Beta-Blocker Pos./Neg. | ID# | Chemical Name | Beta-Blocker Pos./Neg. |
|---|---|---|---|---|---|
| 1 | Acetylsalicylic Acid | Neg. | 30 | Methadone (DL-) | Neg. |
| 2 | Alprazolam | Neg. | 31 | Morphine Sulfate | Neg. |
| 3 | Amobarbital | Neg. | 32 | Nalorphine | Neg. |
| 4 | Ampicillin | Neg. | 33 | Naproxen | Neg. |
| 5 | Phenethylamine (beta-) | Neg. | 34 | Niacinamide | Neg. |
| 6 | Benzoylecgonine | Neg. | 35 | Penicillin | Neg. |
| 7 | Butalbital | Neg. | 36 | Pentobarbital | Neg. |
| 8 | Caffeine | Neg. | 37 | Phencyclidine | Neg. |
| 9 | Chlordiazepoxide | Neg. | 38 | Phenobarbital | Neg. |
| 10 | Chlorpromazine | Neg. | 39 | Phenylephrine | Neg. |
| 11 | Clonazepam | Neg. | 40 | Phenylpropanolamine | Neg. |
| 12 | Clorazepate | Neg. | 41 | Procainamide | Neg. |
| 13 | Cocainethylene | Neg. | 42 | Procaine | Neg. |
| 14 | Cocaine | Neg. | 43 | Pseudoephedrine | Neg. |
| 15 | Codeine | Neg. | 44 | Quinidine | Neg. |
| 16 | Amphetamine (D-) | Neg. | 45 | Temazepam | Neg. |
| 17 | Methamphetamine (D-) | Neg. | 46 | Theophylline | Neg. |
| 18 | Dextromethorphan | Neg. | 47 | Zomepirac | Neg. |
| 19 | Fenoprofen | Neg. | 48 | Ephedrine Hydrochloride (1R,2S)-(-) | Neg. |
| 20 | Gemfibrozil | Neg. | 49 | Ecgonine Methyl Ester Hydrochloride | Neg. |
| 21 | Gentisic Acid | Neg. | 50 | Ecgonine Hydrochloride | Neg. |
| 22 | Hydrocodone | Neg. | 51 | Diazepam | Neg. |
| 23 | Hydromorphone | Neg. | 52 | PCP | Neg. |
| 24 | Ibuprofen | Neg. | 53 | (-)-11-NOR-9-Carboxy-Delta9-THC | Neg. |
| 25 | Imipramine | Neg. | 54 | Morphine | Neg. |
| 26 | Ephedrine (L-) | Neg. | 55 | (-)-Cotinine | Neg. |
| 27 | Methamphetamine (L-) | Neg. | | | |
| 28 | Lidocaine | Neg. | | | |
| 29 | Meperidine | Neg. | | | |

The samples were tested three times, following the procedures used in Example 3. All 55 samples produced a negative test result. Thus, the immunoassay of the present invention is specific to beta blockers.

EXAMPLE 7

Cross-Reactivity

Cross-reactivity among beta blockers was tested using urine samples spiked with individual beta blockers. Each sample contained 10 μg/ml of a single beta blocker. The samples were tested following the procedures used in EXAMPLE 3. The results are set forth in the following table:

| Beta-Blocker Name | Spiked Conc. (μg/ml) | Positivity/Negativity Results (P ≧ 5.0 μg/ml) |
|---|---|---|
| Atenolol | 10.0 | P |
| Metoprolol | 10.0 | P |
| Propranolol | 10.0 | P |
| Bisoprolol | 10.0 | P |
| Pindolol | 10.0 | P |
| Levatol | 10.0 | N |
| Labetalol | 10.0 | N |
| Acebutolol | 10.0 | N |
| Carteolol | 10.0 | N |
| Nadolol | 10.0 | N |
| Timolol | 10.0 | N |
| Sotalol | 10.0 | N |

The immunoassay of the present invention detected 5 of the 12 most commonly prescribed beta blockers when present at 10 μg/ml. Thus, the single immunoassay of the present invention is able to detect multiple beta blockers.

From the foregoing it will be seen that this invention is well adapted to attain all ends and objectives herein-above set forth, together with the other advantages which are obvious and which are inherent to the invention.

Since many possible embodiments may be made of the invention without departing from the scope thereof, it is to be understood that all matters herein set forth, including the Examples, are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. An immunogen having the structure:

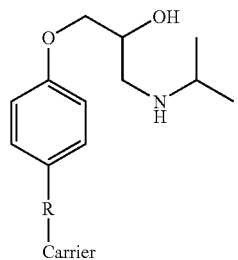

wherein Carrier is an immunogenic carrier material, and wherein R is a linkage.

2. The immunogen of claim 1, wherein said immunogenic carrier is a protein.

3. The immunogen of claim 1, wherein R is a linking group.

4. The immunogen of claim 3, wherein R is —$(CH_2)_n$COO—, and wherein n is an integer between 0 and about 1,000.

5. The immunogen of claim 4, wherein R is —$CH_2COO$—.

6. An antibody prepared against the immunogen of claim 1.

7. An antibody prepared against the immunogen of claim 5.

8. An immunoassay reagent comprising the antibody of claim 6.

9. An immunoassay reagent comprising the antibody of claim 7.

10. An immunoassay kit, comprising:
an antibody having binding specificity for two or more beta blockers; and
one or more reagents for detecting a complex of said antibody and said beta blockers,
wherein said antibody is obtained using an immunogen having the structure:

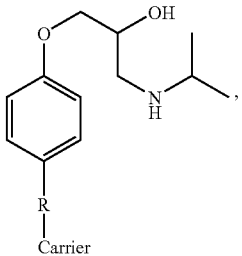

wherein Carrier is an immunogenic carrier material and R is a linkage.

11. The immunoassay kit of claim 10, wherein said reagents comprise a reagent selected from the group consisting of an enzyme, a radioisotope, a fluorescent reagent, a luminescent reagent and a chemiluminescent reagent.

12. The immunoassay kit of claim 10, wherein said reagents comprise an enzyme-beta blocker conjugate and a substrate for said enzyme.

13. The immunoassay kit of claim 10, wherein said antibody is bound to a solid surface and wherein said reagents comprise an enzyme-beta blocker conjugate.

14. An immunoassay method for detecting one or more beta blockers in a sample comprising the steps of:
obtaining a fluid sample;
exposing said fluid sample to an antibody specific to two or more beta blockers, said antibody prepared against an immunogen having the following structure:

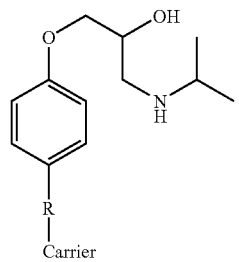

wherein Carrier is an immunogenic carrier material and R is a linkage; and
determining whether said antibody binds to the contents of said sample, said binding being an indication that said sample contains said beta blockers.

15. The method of claim 14 R is a linking group.

16. The method of claim 15, wherein R is —$CH_2COO$—.

17. The method of claim 14, wherein said determining step comprises performing an enzyme immunoassay.

18. The method of claim 17, wherein said enzyme immunoassay is selected from the group consisting of homogeneous enzyme immunoassay and ELISA.

19. The method of claim 14, wherein said beta blockers are selected from the group consisting of Pindolol, Atenolol, Bisoprolol, Metoprolol and Propranolol.

20. The method of claim 14, wherein said sample is a physiological sample.

21. The method of claim 20, wherein said sample is a urine sample.

22. A method for producing an antibody specific to two or more beta blockers comprising the steps of:
injecting an animal with an immunogen having the following formula:

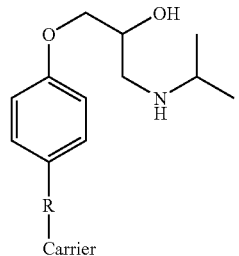

wherein Carrier is an immunogenic carrier material and R is a linkage; and
collecting an antibody produced by said animal in response to said immunogen.

* * * * *